(12) United States Patent
Horner

(10) Patent No.: US 10,076,448 B2
(45) Date of Patent: Sep. 18, 2018

(54) TARSUS EYELID PATCH

(71) Applicant: Nathan Horner, Los Angeles, CA (US)

(72) Inventor: Nathan Horner, Los Angeles, CA (US)

( * ) Notice: Subject to any disclaimer, the term of this patent is extended or adjusted under 35 U.S.C. 154(b) by 27 days.

(21) Appl. No.: 14/868,326

(22) Filed: Sep. 28, 2015

(65) Prior Publication Data

US 2016/0175160 A1 Jun. 23, 2016

Related U.S. Application Data

(63) Continuation-in-part of application No. 14/264,009, filed on Apr. 28, 2014.

(51) Int. Cl.
*A61F 9/04* (2006.01)
*A61F 13/12* (2006.01)
*A61F 13/02* (2006.01)

(52) U.S. Cl.
CPC .............. *A61F 13/124* (2013.01); *A61F 9/04* (2013.01); *A61F 13/025* (2013.01); *A61F 13/0243* (2013.01)

(58) Field of Classification Search
CPC ...................... A61F 13/124; A61F 9/04; A61F 2013/00497; A61F 2013/00502; A61F 9/007; A61F 13/0243; A61F 13/025
USPC ................................. 128/858; 602/47, 52, 74
See application file for complete search history.

(56) References Cited

U.S. PATENT DOCUMENTS

| | | | |
|---|---|---|---|
| 2,527,947 A * | 10/1950 | Loos | A61F 9/04 128/858 |
| 3,068,863 A | 12/1962 | Bowman | |
| 4,867,146 A * | 9/1989 | Krupnick | A61F 9/00 128/858 |
| 5,887,590 A | 3/1999 | Price | |
| 6,034,293 A * | 3/2000 | Stamler | A61F 9/04 128/858 |
| 6,899,104 B1 | 5/2005 | Inman et al. | |
| RE39,896 E | 10/2007 | Arnold et al. | |
| 2002/0100481 A1 * | 8/2002 | Abbasi | A61F 9/04 128/858 |
| 2015/0122265 A1 | 5/2015 | Horner | |

OTHER PUBLICATIONS

U.S. Appl. No. 14/264,009, filed Apr. 28, 2014 (which is owned by the Applicant, Nathan Horner, of the present application), and its prosecution history, including without limitation Office Actions, Amendments, Remarks, prior art references, and other potentially relevant documents or statements.

(Continued)

*Primary Examiner* — Kari Rodriquez
(74) *Attorney, Agent, or Firm* — Proven Patents Law Firm; Kregg Koch

(57) ABSTRACT

A Tarsus Eyelid Patch and method to hold a superior tarsus in a closed position to heal or treat defects on the eye surface is presented. A perforated mesh device includes a medial edge, a lateral edge, a superior edge, an inferior edge, and an adhesive surface, wherein the perforated mesh device is a non-rigid device. The adhesive surface of the superior edge is configured to attach to a region below an eyebrow and on the superior tarsus forming a convex region and further configured to attach to and conform to the superior tarsus when the superior tarsus is in the closed position forming a concave region when the adhesive surface of the inferior edge is to attached to a lower portion of the superior tarsus when the superior tarsus is in the closed position.

19 Claims, 15 Drawing Sheets

(56) References Cited

OTHER PUBLICATIONS

3M Nexcare Flexible 1 inch Clear Tape, 20 YD Value Pack. Applicant submits that this product was in public use prior to the Applicant's filing date.

U.S. Appl. No. 14/264,009, now abandoned, filed Apr. 28, 2014, inventor/applicant Nathan Horner, and its prosecution history, including without limitation Office Actions, amendments, remarks, cited references, and any other potentially relevant documents. U.S. Appl. No. 14/264,009 is a parent application of the present application.

\* cited by examiner

TARSUS EYELID PATCH

CROSS REFERENCE TO RELATED APPLICATIONS

This application is a Continuation-in-Part to U.S. application Ser. No. 14/042,736, filed Nov. 6, 2013, and application Ser. No. 14/264,009 filed Apr. 28, 2014 which are hereby incorporated by reference.

FIELD OF INVENTION

The present invention relates to a device for aiding the healing of an eye after injury or a medical procedure. More specifically, the present invention relates to a device for holding an eyelid in a closed position while allowing the eye lid to breathe and providing an opening for inserting medicine into the closed eye.

BACKGROUND

There has long been a clinical need for a device to hold an upper eyelid in a closed position for healing after various surgeries or injuries. Tarsorrhaphy is a surgical procedure of sewing the eyelid closed. As illustrated in FIG. 1 (prior art), an upper eyelid is sewn together with the bottom eyelid to keep the eye closed during a healing period.

Other prior-art methods of holding the eyelid closed include the standard cloth eye patch which smothers the eye having a different purpose design and method, illustrated in FIG. 2 (prior-art), and medical tape, both being uncomfortable and are not effective for keeping the eye closed. Therefore, eye doctors commonly use a Tarsorrhaphy as the standard method of keeping the eyelid closed.

Still other prior-art methods for holding an eyelid closed for eye healing has featured a substantially rigid eye splint, as disclosed in U.S. Pat. No. 6,034,293 to John F. Stamler. The rigid eye splint has proved to be uncomfortable for the user wearing the device as well as an antiquated method.

Accordingly, there is a need for an innovative technically advanced device that heals defects on an eyes surface by painlessly and comfortably holding the upper eyelid down thereby keeping the eye closed, and making the eyelid the eye's natural bandage.

BRIEF SUMMARY OF THE INVENTION

The Tarsus Eyelid Patch holds an eye in a closed position to heal defects on the eye surface.

The device includes a medial edge, a lateral edge, a superior edge, an inferior edge, and an adhesive surface, wherein, the perforated mesh device is a non-rigid device, wherein the adhesive surface of the superior edge is configured to attach to the region below an eyebrow on a superior tarsus forming a convex curve and further configured to attach to and conform to the superior tarsus when the superior tarsus is in the closed position forming a concave curve, and wherein when the non-rigid device forms the concave curve and the convex curve when the superior tarsus is in the closed position, the multiple curvatures adds strength and stiffness to hold the superior tarsus in the closed position.

It is contemplated that the device of the present invention further includes the medial edge and the lateral edge configured to expose a medial and lateral canthus of the eye respectively when the adhesive surface of the device is attached to the superior tarsus when the superior tarsus is in the closed position, wherein the device allows a medication insertion into the exposed medial and lateral canthus of the eye when the adhesive surface of the device is attached to the superior tarsus when the superior tarsus is in the closed position.

It is contemplated that the perforated mesh device of the present invention is made of a 2-ply material from at least one of: a mesh fabric material; a hypoallergenic plastic material; and a latex free tape material.

A method for holding a superior tarsus of an eye in a closed position is presented, comprising the steps of applying a tarsus eyelid patch to a region below an eyebrow on a superior tarsus when the superior tarsus is in the closed position forming a convex curve; conforming and attaching the tarsus eyelid patch to a lower portion of the superior tarsus when the superior tarsus is in the closed position forming a concave curve; adhering the tarsus eyelid patch to the region below the eyebrow on the superior tarsus, and to the lower portion of the superior tarsus; exposing a medial and lateral canthus of the eye respectively when the superior tarsus is in the closed position; and allowing a medication insertion into the medial and lateral canthus of the eye when the superior tarsus is in the closed position; wherein when the superior tarsus is in the closed position, the applied tarsus eyelid patch is concave in a horizontal direction in the region below the eyebrow on the superior tarsus, and the tarsus eyelid patch is convex in a vertical direction over the closed superior tarsus making the tarsus eyelid patch stiff and holding the superior tarsus in the closed position.

DETAILED DESCRIPTION AND BEST MODE OF IMPLEMENTATION

Figure 1:
FIG. 1 (prior-art) Shows a front view photograph of actual Tarsorrhaphy procedure where the eyelids are sewn closed.
Figure 2:
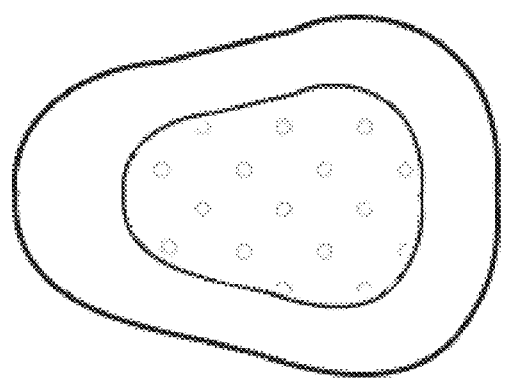
FIG. 2 (prior-art) Shows a standard cloth eye patch.
Figure 3:
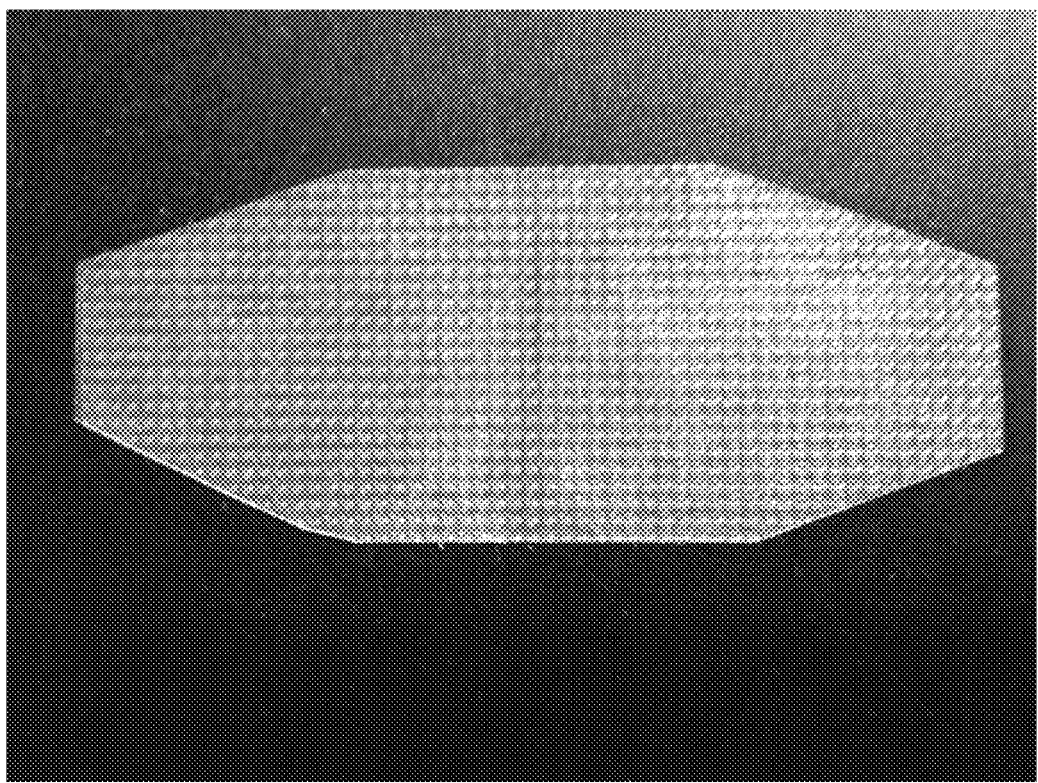
FIG. 3 Shows a photograph of the Tarsus Eyelid Patch device of the present invention.
Figure 4:
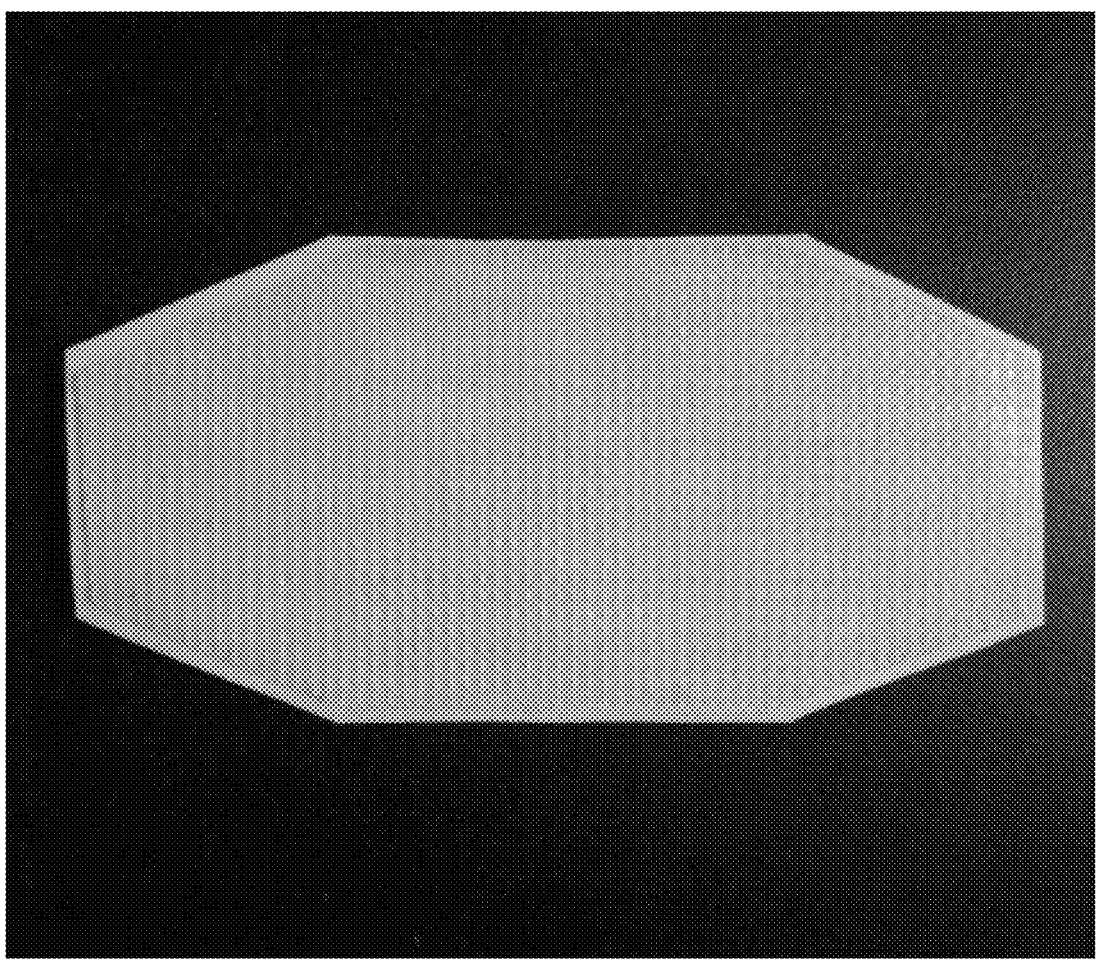
FIG. 4 Shows a photograph of the Tarsus Eyelid Patch device of the present invention on a release liner.
Figure 5:
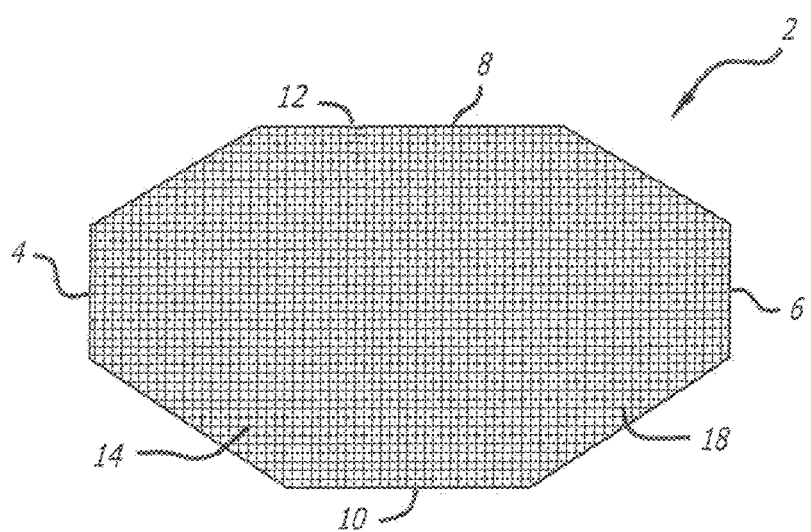
FIG. 5 Presents a drawing of the Tarsus Eyelid Patch of the present invention.
Figure 6:
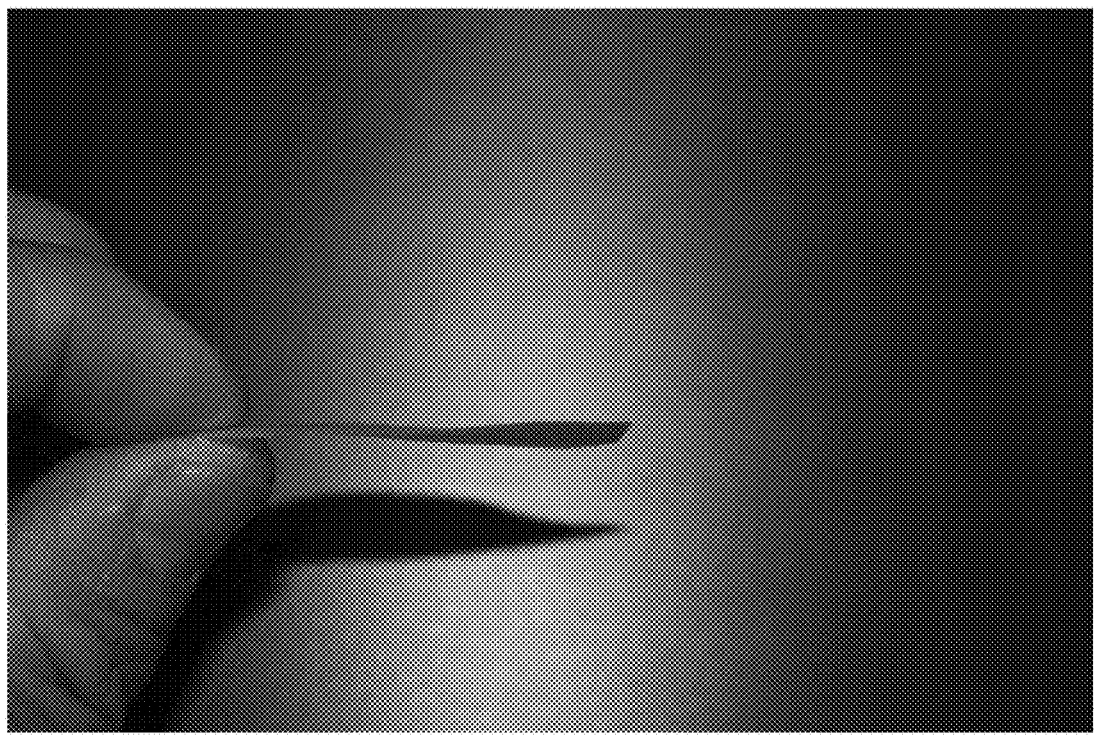
FIG. 6 Shows a side view photograph of the Tarsus Eyelid Patch of the present invention, to illustrate an approximate thickness of 2 ply material.
Figure 7:
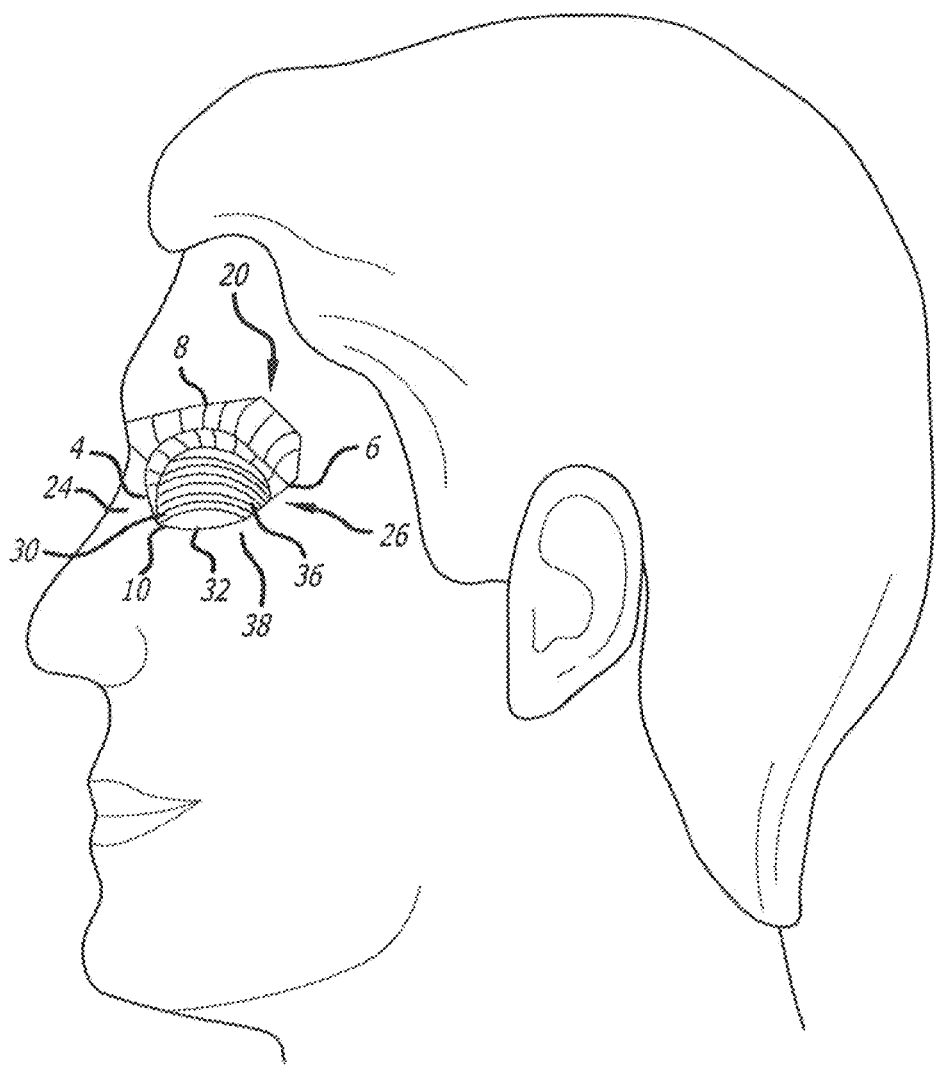
FIG. 7 Presents a profile view drawing of the applied Tarsus Eyelid Patch of the present invention.
Figure 8:
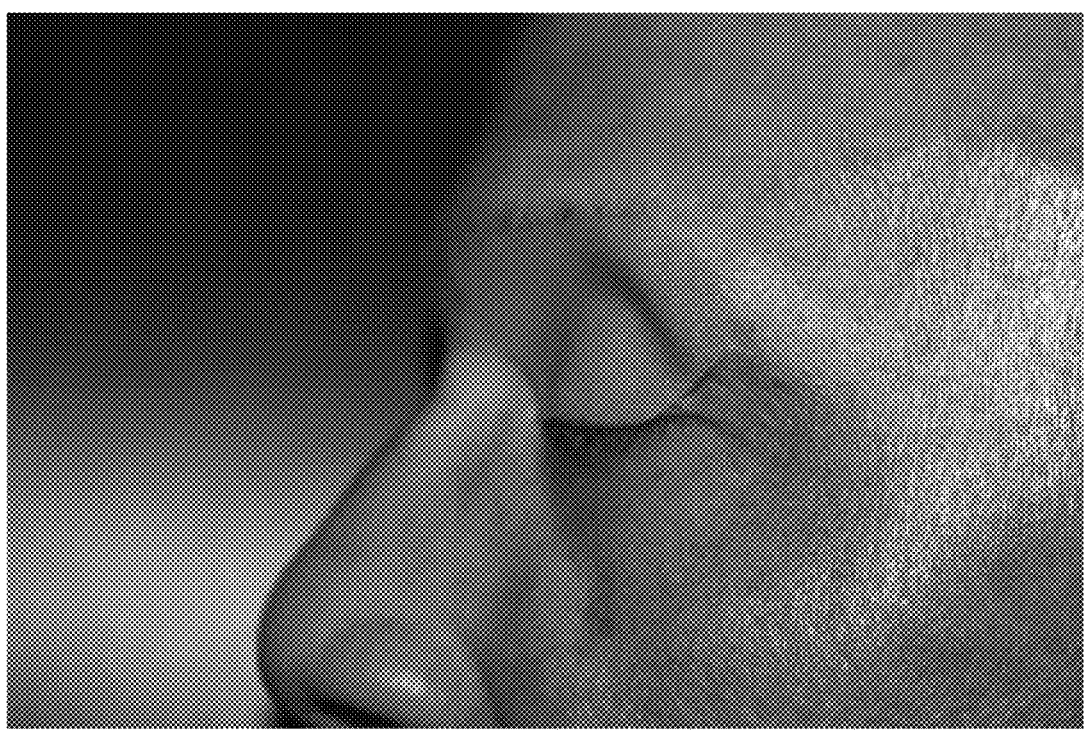
FIG. 8 Shows a front view photograph of the applied Tarsus Eyelid Patch of the present invention.

The Tarsus Eyelid Patch heals defects on an eye's surface, as a painless option to Tarsorrhaphy, a standard surgical procedure of sewing the eyelids closed, illustrated in FIG. 1 (prior art), by painlessly and comfortably holding the upper eyelid or superior tarsus down, and holding the eye closed.

In the anatomy of the eye, the flat of the eyelid is called the tarsus. The eyelids protect and help lubricate the eyes. The eyelid skin itself is very thin, containing no subcutaneous fat, and is supported by a tarsal plate. This tarsal plate is a fibrous layer that gives the lids shape, strength, and a place for muscles to attach.

The tarsi or tarsal plates are two comparatively thick, elongated plates of dense connective tissue, about 2.5 cm (1.0 in) in length, one is found in each eyelid and contributes to its form and support. They directly abut the lid margins. The tarsus has a lower and upper part making up the palpebrae. The superior tarsus, tarsus superior or superior tarsal plate, the larger, is of a semilunar form, about 10 mm (0.4 in) in breadth at the center, and gradually narrowing toward its extremities. It is adjoined by the superior tarsal muscle to the anterior surface of this plate the aponeurosis of the levator palpebrae superioris is attached.

The inferior tarsus, tarsus inferior or inferior tarsal plate, is smaller than the superior tarsus. It is thin, and elliptical in form, and has a vertical diameter of about 5 mm (0.2 in). The free or ciliary margins of these plates are thick and straight.

The angle formed by the meeting of the upper and lower eyelids or superior tarsus and inferior tarsus, at either side of the eye is defined as the canthus. The medial canthus is the corner formed near the nose bridge. The lateral canthus is the corner formed distal the nose bridge.

The present invention comprises improved procedures and articles for medically treating an eye after various surgeries or injuries, and for maintaining the health of the eye in the case of many other eye issues, including but not limited to nocturnal use to hold the eye in a closed position in matters of dry eye, lazy eye, and strokes. It will be appreciated by those in the art that anesthesiologist will use the tarsus eyelid patch during non-eye related surgeries and medical procedures where anesthesia renders a patient unconscious and a need arises to keep the anesthetized patient's eyes closed.

As illustrated in the accompanying photographs and drawings, the perforated mesh device of the present invention, designated by reference numeral 2-18, is designed for comfortably holding an eye in a closed position. The eye and other eye features are designated by reference numerals 20-38. Photographs and drawings consisting of FIGS. 3-15 display a preferred embodiment of the present invention. The mesh device 2 includes a first edge 4 for insertion into an eye socket 22 medial canthus 24 of a user's face. A lateral edge 6 or distal edge, of the mesh device 2 of the present invention is opposite the medial edge 4. The mesh device further includes an adhesive surface 12 (referenced to but not shown), a non-adhesive surface 14, a superior edge 8, and an inferior edge 10.

As illustrated in FIGS. 7-15, the superior edge 8 of the mesh device 2 is inserted onto the eye socket 22 below the eyebrow 34 and the mesh device bottom edge/inferior edge 10 is inserted onto the user's upper eyelid 30 above the inferior tarsus 32. The mesh device adhesive surface 12 adheres the mesh device 2 to the eye socket 22, and more specifically to the superior tarsus 30. The mesh device non-adhesive surface 14 does not contact the eye socket 22 nor the superior tarsus 30.

In the accompanying photographs and drawings the mesh device 2 is positioned on the user's left eye with medial edge 4/nose corner edge 4 being placed on the left side of the user's face. However, it should be appreciated that the device is interchangeable for use on both the left and right sides of the user's face. When using the mesh device on the right eye, the reference numerals 4 and 6 may be interchanged to depict that the medial edge/nose corner edge 4 of the present device is inserted onto the user's right facial area.

Figure 15:
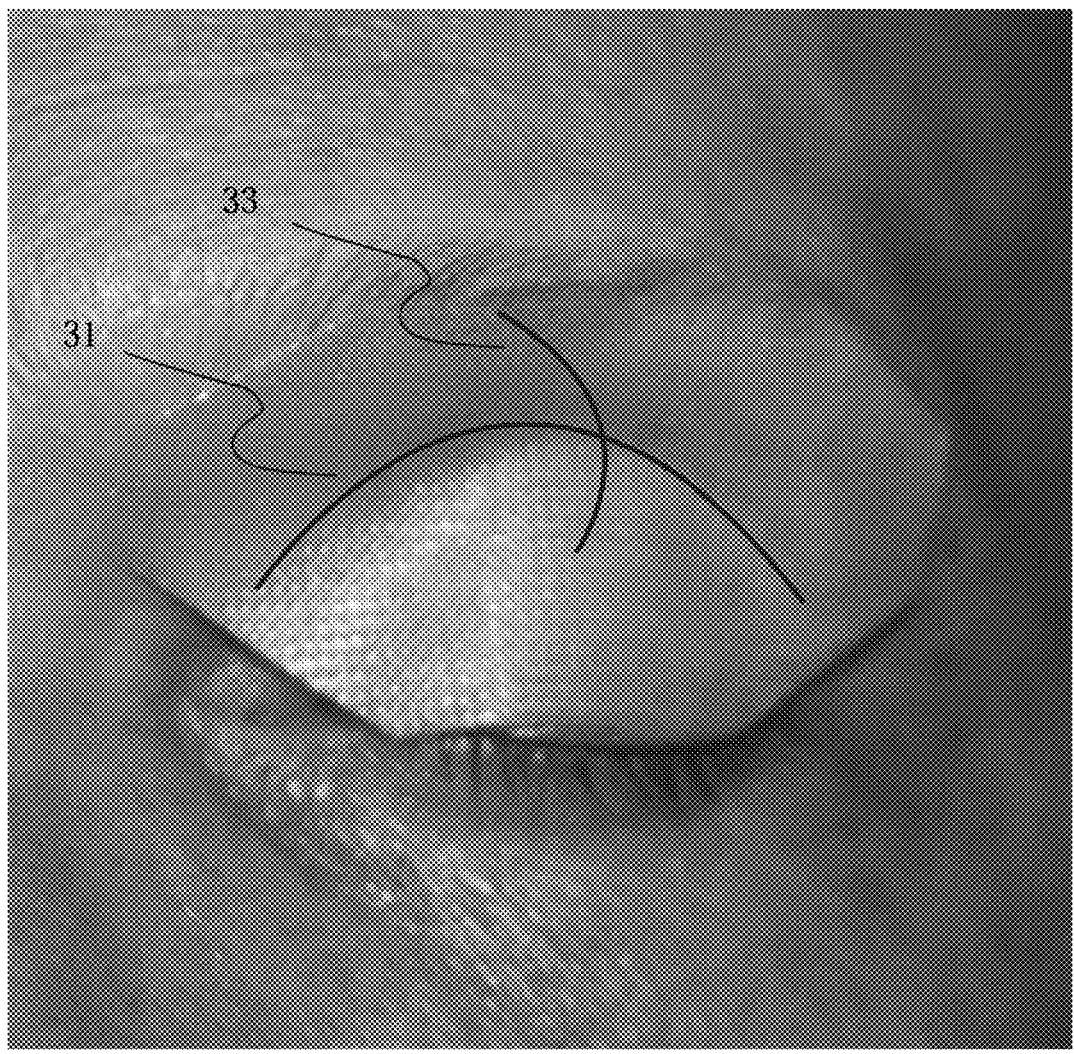
FIG. 15 Shows a front view photograph of the Tarsus Eyelid Patch applied on the eye.

As shown in the photograph labeled FIG. 15, the mesh device becomes concave when conforming to the eye socket. This in turn curves the lower portion of the mesh material forcing the eyelid down and making the device act like the corrugation in steal, adding strength to the device, while achieving its function to hold the eyelid in a closed position. The mesh device 2 upper material, superior edge, rolls convexly around the under brow and on the superior tarsus. The mesh device 2 lower material, inferior edge, assumes the contour shape of the eyeball giving the device curvature 36, holding the superior tarsus 30 in the closed position. See FIGS. 8, 9, 13, and 15.

It is well known that adding curvature to a flexible surface adds strength and rigidity. Notable examples are making stiff cardboard from paper and Pringles® potato chips stored in cans. Here, the tarsus eyelid patch achieves curves when affixed to the region of the eye sockets below the eyebrow and to the closed eyelid. When affixed, the tarsus eyelid patch is concave in the horizontal direction in the region between the eyebrow and the upper eyelid, and the eyelid tarsus patch is convex in the vertical direction over the closed superior tarsus.

The union of a convex and a concave curves forms a hyperbolic paraboloid curve.

A hyperbolic paraboloid surface gains strength and rigidity by balancing the compressive forces of the convex region with the tensile forces of the concave region. A hyperbolic paraboloid surface is characterized by having vertical parabolic cross sections and horizontal hyperbolic cross sections.

Figure 10:
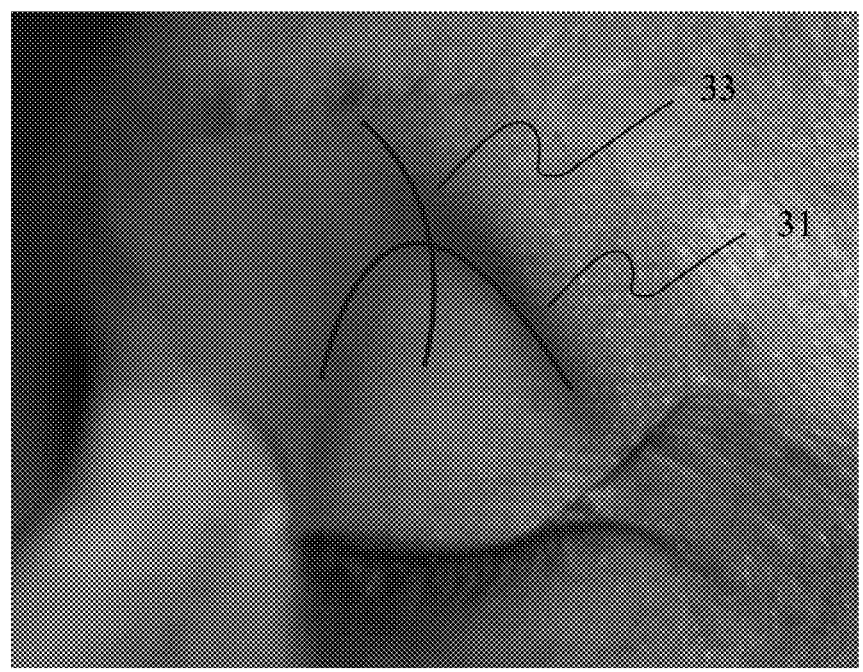
FIG. 10 Shows a side profile photograph of the Tarsus Eyelid Patch applied close up on the eye.

Referring now to FIGS. 10 and 15, the convex region 31 and the concave region 33 are illustrated when the eyelid tarsus patch is affixed.

The mesh device 2 may be made of two 1-ply material sheets of transpore plastic, hypoallergenic, adhesive, perforated, transparent, latex-free tape. Thou it would be molded as one piece, and could be made out of other perforated adhesive medical material. For example, the preferred embodiment of the present invention may be constructed from a 2-ply medical material of at least one of a mesh fabric material, a hypoallergenic plastic material, or a latex free tape material, all having an adhesive surface.

As shown in photographs FIG. 3, FIG. 3, FIG. 8, FIG. 10, FIG. 13, and FIG. 15, the mesh device 2 is designed with angles so the corners of the eyes are exposed for comfort, and to add medicine when the eyelid is closed, as to be noninvasive to the eye opening. As illustrated in the FIG. 1A, FIG. 1B, FIG. 1D, and FIG. 3D, in an embodiment of the invention, the perforation or mesh of the thin material allows the user's eyelid, exterior skin on the superior tarsus, to breathe.

In a preferred embodiment of the present invention, the mesh device 2 dimensions are 2.25" length×1" height× 0.0135" thickness. Metric measurements may be 5.7 cm length×2.5 cm height×34 mm thickness. However, it should be appreciated that the measurements and dimensions may vary to adapt to a specific user's facial features. The material is easily cut for adjustments if needed. The adhesive holds strong, yet it allows the device to be easily removed.

Figure 13:
FIG. 13 Shows a front view photograph of the applied device.

In application of the mesh device 2, the user centers it over the closed superior tarsus, as shown in FIG. 13 and FIG. 15. The user then lines up the device inferior edge 10 just above the center of the opening of the eye on the upper eye lid above the lash. The user then gently rub the device 2 onto the eyelid, around the radius of the eyeball and up into the socket 20 and over the under part of the eyebrow 34 adhering the device 2 to the superior tarsus 30. This application holds down the superior tarsus only, keeping the eye closed.

Figure 9:
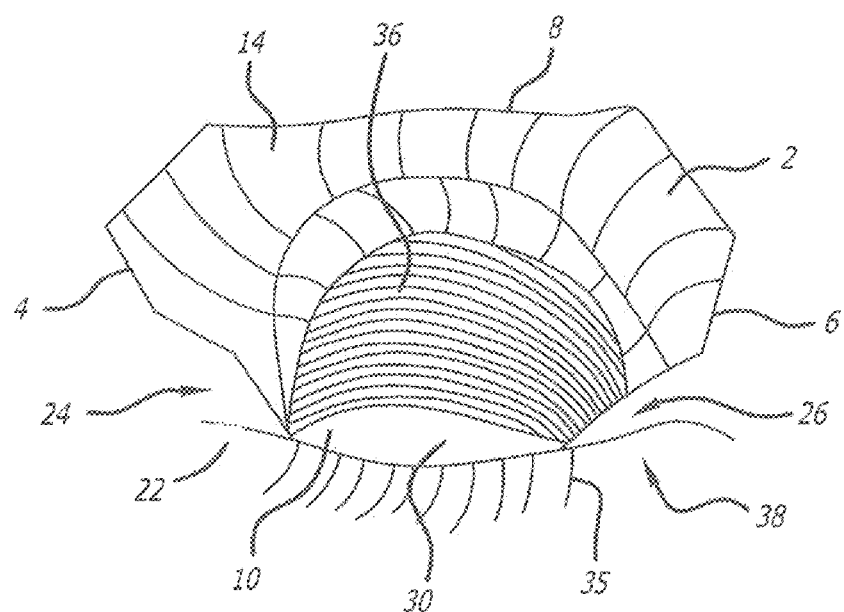
FIG. 9 Illustrates a detailed profile view of the Tarsus Eyelid Patch applied on the eye, displaying how the device functions to hold the eyelid down and how the device conforms to the eye socket, and under brow, leaving the corners of the eyes exposed.
Figure 11:
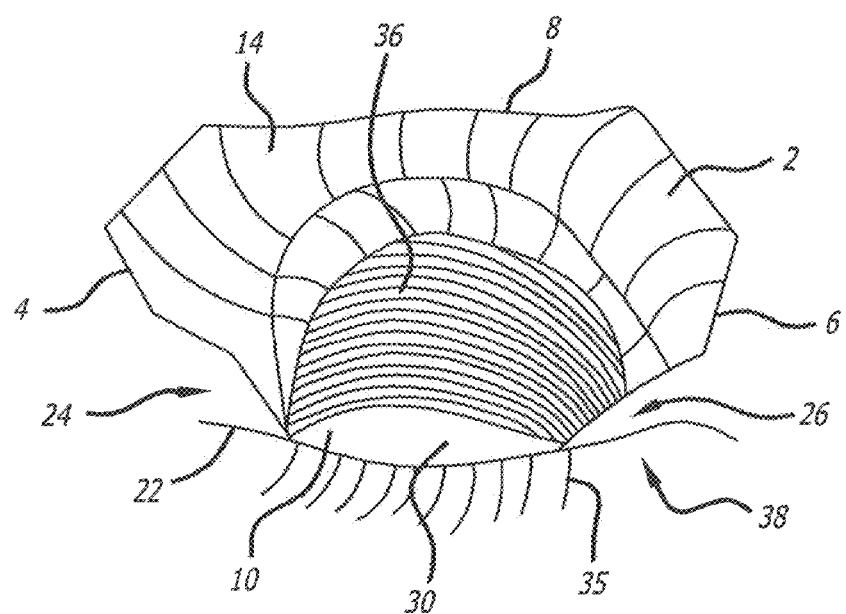
FIG. 11 Illustrates a detail profile view of the Tarsus Eyelid Patch applied on an eye, displaying how the upper material of the device rolls convexly around the under brow and forms to the eye socket and conforms to the radius of the eye.
Figure 12:
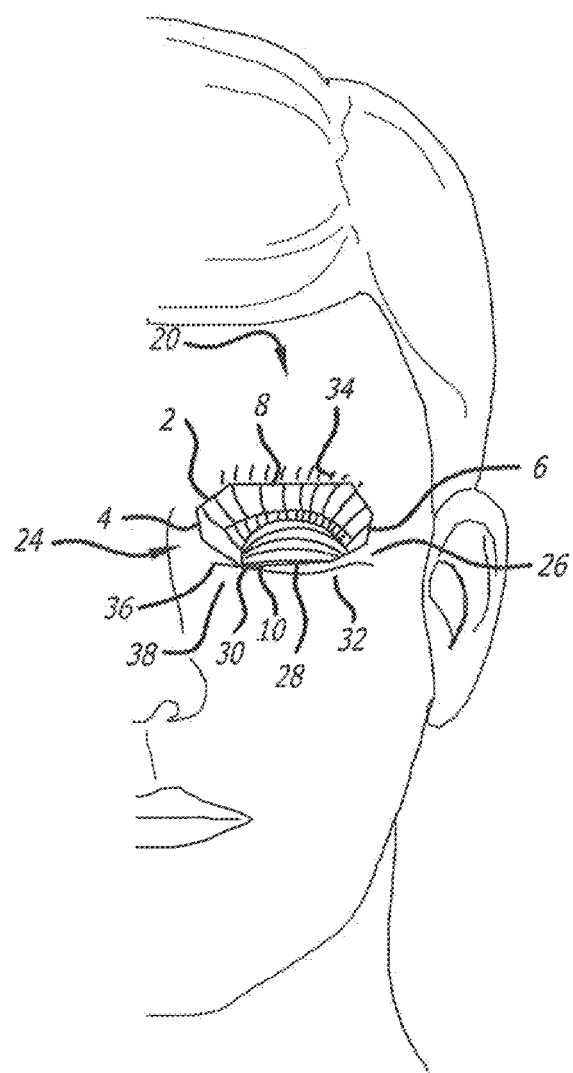
FIG. 12 Illustrates a front view of the applied device.
Figure 14:
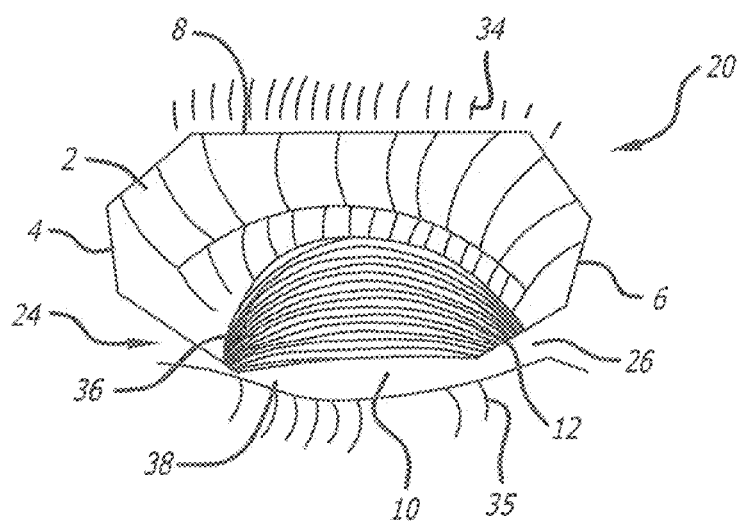
FIG. 14 Illustrates a front view drawing of the Tarsus Eyelid Patch applied on an eye, and that the device is applied just above the opening of the eye on the upper eyelid.

FIGS. 9, 11, 14 illustrate a detailed profile view of the Tarsus Eyelid Patch device applied on the eye, displaying how the device functions to hold the eyelid closed, and how the device conforms to the eye socket and under brow, leaving the corners of the eye exposed, and being noninvasive to the eye opening or to the inferior tarsus.

In the preferred embodiment of the present invention, the mesh device 2 will be packaged individually like a bandage which will make it possible to be used in rural areas and third world countries. The present invention is ideal for use by the military for treating eye injuries during combat. Each device is intended for one time use. It may be worn daily, but also may be worn at night while sleeping as in cases of chronic dry eye, lazy eye, stroke, and for general eye health.

The device is affective to heal scratches and defects on the eyes surface, also to aid in healing after Lasik and or eye surgeries with a doctor's recommendation. The mesh device 2 of the present invention is ideal for the elderly and children, and if necessary is easily applied by a caregiver. The tarsus eyelid patch will be produced in various sizes for youths, adults, and for adaptation to all shapes and forms of eyes, due to varying facial characteristics and ethnicities. This device relieves unnecessary suffering.

The foregoing description of preferred embodiments is presented for purposes of illustration and description. Furthermore, the description is not intended to limit the invention to the form disclosed herein. Accordingly, variants and modifications consistent with the following teachings, and skill and knowledge of the relevant art, are within the scope of the present invention.

I claim:

1. A method for holding a superior tarsus of an eye in a closed position using a tarsus eyelid patch, comprising:
    applying a first main surface of the eyelid patch against an upper eyelid having eyelashes when the upper eyelid is in a closed position such that an inferior edge of the eyelid patch is positioned above the eyelashes of the upper eyelid, the first main surface having an adhesive thereon and comprising a first portion, a second portion, and a third portion;
    forming a first curvature in the first portion of the first main surface of the eyelid patch by conforming the first portion of the eyelid patch to the upper eyelid when the upper eyelid is in the closed position;
    forming a second curvature in the second portion of the eyelid patch by conforming the second portion of the eyelid patch to an eye socket;
    forming a third curvature in the third portion of the first main surface of the eyelid patch by conforming the third portion of the first main surface of the eyelid patch to an under brow below an eyebrow and above the upper eyelid and second portion;

wherein:
        the second curvature is formed in an opposite direction as compared to the first curvature;
        the tarsus eyelid patch is concave in a horizontal direction in a region between the eyebrow and the upper eyelid, and the tarsus eyelid patch is convex in the vertical direction over the closed superior tarsus so as to form a hyperbolic paraboloid curve; and
        forming the hyperbolic paraboloid curve stiffens the tarsus eyelid patch to effectively hold the upper eyelid in the closed position.

2. The method of claim 1, wherein:
    the eyelid patch further comprises a medial edge, a lateral edge, and a superior edge; and
    wherein the medial edge and the lateral edge are configured to expose the medial and lateral canthus of the eye when the first main surface of the eyelid patch is attached to the eyelid when the eyelid is in the closed position.

3. The method of claim 2, further comprising gently rubbing the tarsus eyelid patch on the region below the eyebrow and to the upper eyelid, including a lower portion of the upper eyelid.

4. The method of claim 1, wherein when the first curvature is a convex curve and the second curvature is a concave curve when the upper eyelid is in the closed position, the convex and concave curves in the eyelid patch add strength and stiffness to hold the upper eyelid in the closed position.

5. The method of claim 1, further comprising adapting the eyelid patch to be attached to various eye shapes and formations by cutting the tarsus eyelid patch for adjustments.

6. The method of claim 1, wherein the eyelid patch is made of at least one of a mesh fabric material, a hypoallergenic plastic material, and a latex free tape material.

7. The method of claim 1, wherein the eyelid patch is configured to expose a medial and lateral canthus of the eye when the eyelid patch is over the upper eyelid and the upper eyelid is in the closed position.

8. A method for holding an upper eyelid in a closed position, comprising:
    adhering an eyelid patch having adhesive on at least one surface thereof to an outer surface of skin of the upper eyelid, an outer surface of skin of an under brow, and to an outer surface of skin over an eye socket when the upper eyelid is in the closed position, the eyelid patch having a superior edge at an upper portion thereof, an inferior edge at a lower portion thereof, a medial edge at a first side of the patch, a lateral edge at a second, opposite side of the patch, and a middle portion between the upper portion and the lower portion;
    positioning the inferior edge of the eyelid patch above the user's eyelashes so that the eyelid patch does not cover the user's eyelashes;
    positioning the superior edge of the eyelid patch below the user's eyebrow so that the eyelid patch does not cover the user's eyebrow;
    conforming the middle portion of the eyelid patch to the outer surface of the skin over the eye socket so as to form a concave curve in a horizontal direction, wherein the eye socket is between the under brow and the upper eyelid;
    conforming the lower portion of the eyelid patch to the outer surface of the skin of the upper eyelid so as to form a convex curve in a vertical direction over the upper eyelid; and
    conforming the upper portion of the eyelid patch to the outer surface of the skin of the under brow, the outer surface of the skin of the under brow being between the user's eyebrow and the outer surface of skin of the upper eyelid;

wherein:

conforming the middle portion of the eyelid patch to the outer surface of the skin over the eye socket so as to form a convex curve in a horizontal direction and conforming the lower portion of the eyelid patch to the outer surface of the skin of the upper eyelid so as to form a convex curve in a vertical direction over the upper eyelid forms a hyperbolic paraboloid curve which stiffens the eyelid patch to hold the upper eyelid in the closed position.

9. The method of claim 8, wherein the eyelid patch comprises a mesh material.

10. The method of claim 8, wherein the eyelid patch comprises an adhesive backed hypoallergenic plastic material.

11. The method of claim 8, further comprising adapting the eyelid patch to be attached to various eye shapes and formations by cutting the tarsus eyelid patch for adjustments.

12. The method of claim 8, wherein the eyelid patch is made of at least one of a mesh fabric material, a hypoallergenic plastic material, and a latex free tape material.

13. The method of claim 8, wherein the eyelid patch is configured to expose a medial and lateral canthus of the eye respectively when the eyelid patch is over the upper eyelid and the upper eyelid is in the closed position.

14. A method for holding an upper eyelid in a closed position, comprising:

adhering a lower portion, a middle portion, and an upper portion of a cover member to a user's upper eyelid and under brow;

covering the user's upper eyelid with the lower portion of the cover member without covering eyelashes of the upper eyelid so that a lower edge of the cover member is positioned above the eyelashes of the upper eyelid when the upper eyelid is in the closed position;

covering the user's eye socket with the middle portion of the cover member;

covering the user's under brow with the upper portion of the cover member;

forming a first concave curve in a vertical direction in a middle portion of the cover member by conforming the middle portion of the main surface of the cover member to the user's eye socket;

forming a convex curve in the vertical direction in the upper portion of the cover member by conforming the upper portion of the cover member to the skin of the under brow that is above the eyelid, the upper portion being above the middle portion of the cover member;

forming a second convex curve in a horizontal direction in the lower portion of the cover member, the lower portion being below the middle portion of the cover member;

wherein:

forming the first concave curve, the convex curve, and the second concave curve stiffen the cover member to hold the upper eyelid in the closed position; and the middle portion, the upper portion, and the lower portion of the cover member all have adhesive on at least one surface thereof to adhere the cover member to the user's skin.

15. The method of claim 14, further comprising applying a substance to one or both of the corners of the eye.

16. The method of claim 15, wherein the substance is a medication.

17. The method of claim 14, wherein the cover member has a first cutout at one end of the lower edge and a second cutout at a second end of the lower edge to permit the application of said substance to one or both of the corners of the eye.

18. The method of claim 14, wherein the eyelid patch is configured to expose a medial and lateral canthus of the eye respectively when the eyelid patch is over the eyelid and the eyelid is in the closed position.

19. The method of claim 14, wherein the cover member is made of at least one of a mesh fabric material, a hypoallergenic plastic material, and a latex free tape material.

* * * * *